United States Patent
Peters et al.

(10) Patent No.: US 11,820,723 B2
(45) Date of Patent: Nov. 21, 2023

(54) PRODUCTION OF ALKYLAROMATIC COMPOUNDS

(71) Applicant: ExxonMobil Chemical Patents Inc., Baytown, TX (US)

(72) Inventors: Aaron W. Peters, New Hope, PA (US); William J. Knaeble, Bridgewater, NJ (US); Allen W. Burton, Stewartsville, NJ (US); Ivy D. Johnson, Lawrenceville, NJ (US); Christopher G. Oliveri, Bridgewater, NJ (US); Reuben Britto, Redwood City, CA (US)

(73) Assignee: ExxonMobil Chemicals Patents Inc., Baytown, TX (US)

( * ) Notice: Subject to any disclaimer, the term of this patent is extended or adjusted under 35 U.S.C. 154(b) by 0 days.

(21) Appl. No.: 17/765,024

(22) PCT Filed: Sep. 16, 2020

(86) PCT No.: PCT/US2020/051082
§ 371 (c)(1),
(2) Date: Mar. 30, 2022

(87) PCT Pub. No.: WO2021/076259
PCT Pub. Date: Apr. 22, 2021

(65) Prior Publication Data
US 2022/0371972 A1    Nov. 24, 2022

Related U.S. Application Data

(60) Provisional application No. 62/916,419, filed on Oct. 17, 2019.

(30) Foreign Application Priority Data

Jan. 30, 2020   (EP) .................................... 20154682

(51) Int. Cl.
*C07C 2/66*         (2006.01)
*B01J 29/70*        (2006.01)

(52) U.S. Cl.
CPC .............. *C07C 2/66* (2013.01); *B01J 29/7007* (2013.01); *C07C 2529/06* (2013.01)

(58) Field of Classification Search
CPC ......... C07C 2/66; C07C 15/085; C07C 6/126; C07C 2529/70; B01J 29/7038
See application file for complete search history.

(56) References Cited

U.S. PATENT DOCUMENTS 3,293,192 A    12/1966   Maher et al.
3,308,069 A     3/1967   Wadlinger et al.
(Continued)

FOREIGN PATENT DOCUMENTS

EP    0293032 A2     11/1988
JP    H04-187647 A    7/1992
(Continued)

OTHER PUBLICATIONS

Blasco, T. et al., (1996) "Unseeded synthesis of Al-free Ti-β zeolite in fluoride medium: a hydrophobic selective oxidation catalyst", Chemical communications 20, pp. 2367-2368.
(Continued)

*Primary Examiner* — Sharon Pregler
(74) *Attorney, Agent, or Firm* — Siwen Chen

(57) ABSTRACT

A process for producing a monoalkylated benzene comprises the step of contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the transalkylation catalyst, composition comprises zeolite
(Continued)

beta having an external surface in excess of 350 m2/g as determined by the t-plot method for nitrogen physisorption.

23 Claims, 3 Drawing Sheets

(56) References Cited

U.S. PATENT DOCUMENTS

| | | | |
|---|---|---|---|
| 3,415,736 A | 12/1968 | Julius | |
| 3,442,795 A | 5/1969 | Kerr et al. | |
| 3,449,070 A | 6/1969 | Mcdaniel et al. | |
| 3,702,886 A | 11/1972 | Argauer et al. | |
| 3,709,979 A | 1/1973 | Chu | |
| 3,766,093 A | 10/1973 | Chu | |
| 3,832,449 A | 8/1974 | Rosinski et al. | |
| 3,894,104 A | 7/1975 | Chang et al. | |
| 3,923,636 A | 12/1975 | Mead et al. | |
| 3,950,496 A | 4/1976 | Ciric | |
| 3,972,983 A | 8/1976 | Ciric | |
| 4,016,218 A | 4/1977 | Haag et al. | |
| 4,016,245 A | 4/1977 | Plank et al. | |
| 4,021,947 A | 5/1977 | Shneider | |
| 4,076,842 A | 2/1978 | Plank et al. | |
| 4,234,231 A | 11/1980 | Yan | |
| 4,401,556 A | 8/1983 | Bezman et al. | |
| 4,439,409 A | 3/1984 | Puppe et al. | |
| 4,556,477 A | 12/1985 | Dwyer | |
| 4,826,667 A | 5/1989 | Zones et al. | |
| 4,954,325 A | 9/1990 | Rubin et al. | |
| 5,098,684 A | 3/1992 | Kresge et al. | |
| 5,102,643 A | 4/1992 | Kresge et al. | |
| 5,198,203 A | 3/1993 | Kresge et al. | |
| 5,236,575 A | 8/1993 | Bennett et al. | |
| 5,250,277 A | 10/1993 | Kresge et al. | |
| 5,362,697 A | 11/1994 | Fung et al. | |
| 6,077,498 A | 6/2000 | Diaz et al. | |
| 6,756,030 B1 | 6/2004 | Rohde et al. | |
| 6,936,744 B1 * | 8/2005 | Cheng | C07C 6/126 585/475 |
| 7,713,513 B2 | 5/2010 | Jan et al. | |
| 10,017,394 B2 | 7/2018 | Lai et al. | |
| 2012/0088937 A1 | 4/2012 | Jan et al. | |
| 2013/0183231 A1 | 7/2013 | Senderov et al. | |
| 2013/0197287 A1 * | 8/2013 | Vincent | C07C 7/12 585/323 |
| 2020/0325084 A1 * | 10/2020 | Rivas Cardona | B01J 35/1023 |

FOREIGN PATENT DOCUMENTS

| | | |
|---|---|---|
| TW | 201932437 | 8/2019 |
| WO | 97/17290 A1 | 5/1997 |
| WO | 02/08159 A1 | 1/2002 |
| WO | 2018/140149 A1 | 8/2018 |
| WO | 2018/236471 A1 | 12/2018 |
| WO | 2021/076259 A1 | 4/2021 |

OTHER PUBLICATIONS

Higgins, J. B. et al., (1988) "The framework topology of zeolite beta", Zeolites, vol. 8, No. 6, pp. 446-452.

Newsam, J. M. et al., (1988) "Structural characterization of zeolite beta", Proceedings of the royal society of London. A. mathematical and physical sciences, vol. 420, No. 1859, pp. 375-405.

* cited by examiner

PRODUCTION OF ALKYLAROMATIC COMPOUNDS

CROSS-REFERENCE TO RELATED APPLICATIONS

This application is a US national phase application of PCT Application Serial No. PCT/US2020/051082 having a filing date of Sep. 16, 2020, which claims priority to and the benefit of U.S. Provisional Application No. 62/916,419 having a filing date of Oct. 17, 2019 and European Patent Application No. 20154682.7 having a filing date of Jan. 30, 2020, the disclosures of all of which are incorporated herein by reference in their entireties.

FIELD

The present application relates to a process for producing alkylaromatic compounds, particularly ethylbenzene and cumene.

BACKGROUND

Ethylbenzene and cumene are valuable commodity chemicals which are used industrially for the production of styrene monomer and the coproduction of phenol and acetone, respectively. Ethylbenzene and cumene are typically produced by alkylating benzene with a $C_2$ or $C_3$ alkylating agent, such as ethylene or propylene, under liquid phase or mixed gas-liquid phase conditions in the presence of an acid catalyst, particularly a zeolite catalyst. In addition to the desired monoalkylated product, the process inevitably produces the dialkylated and trialkylated analogs as well as other heavy by-products. Thus, to maximize the yield of ethylbenzene and cumene, it is conventional to transalkylate the polyalkylated products with benzene to generate additional monoalkylated product. The product of the transalkylation reaction is then fed, together with the alkylkation reaction effluent, to one or more benzene columns, to recover unreacted benzene, then to one or more EB or cumene columns, to recover the desired monoalkylated product.

Current state-of-the-art transalkylation zeolite catalysts can convert polyalkylbenzene molecules to ethylbenzene and cumene with high selectivity and activity. However, these catalysts require elevated temperatures, low flow rates of the substrate feed, and large catalyst beds to achieve sufficient conversion, all of which serve to increase process costs. Moreover, the problem is exacerbated by the fact that the trialkylated species are significantly less reactive than the dialkylated species so that, with existing catalysts, it is difficult to find a processing window where effective conversion of the trialkylated species is achieved without adversely affecting the selectivity of the conversion of the dialkylated species.

There is therefore significant interest in providing transalkylation catalysts which can operate at lower temperatures without sacrificing conversion activity and monoalkylated benzene selectivity.

SUMMARY

It has now been found that zeolite beta with a specific high external surface area size is effective over a range of transalkylation conditions to catalyze the reaction of benzene with trialkylbenzenes, particularly triisopropylbenzene, to the monoalkylated species while retaining high selectivity of the conversion of the dialkylated species to the desired monoalkylated species.

In one aspect, the present application relates to a process for producing a monoalkylated benzene comprising the step of contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the transalkylation catalyst composition comprises zeolite beta having an external surface in excess of 350 $m^2/g$ as determined by the t-plot method for nitrogen physisorption.

In a further aspect, the present application relates to a process for producing a monoalkylated benzene, the process comprising:

(a) contacting a feedstream comprising benzene with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene;

(b) separating the alkylation effluent into a first fraction containing monoalkylated benzene and a second fraction containing dialkylated benzene and trialkylated benzene;

(c) contacting at least part of the second fraction with benzene in the presence of a transalkylation catalyst composition under transalkylation conditions effective to convert at least part of the dialkylated benzene and trialkylated benzene to monoalkylated benzene and produce a transalkylation effluent, wherein the transalkylation catalyst composition comprises zeolite beta having an external surface in excess of 350 $m^2/g$ as determined by the t-plot method for nitrogen physisorption; and (d) recovering the monoalkylated benzene from the transalkylation effluent.

In a still further aspect, the present application relates to a transalkylation catalyst composition comprising zeolite beta and having one or more of the following properties:

(i) an external surface in excess of 350 $m^2/g$ as determined by the t-plot method for nitrogen physisorption, (ii) a ratio of external surface area to internal surface area in excess of 0.6, and (iii) a length from 50 nanometers to 150 nanometers, a width from six nanometers to 15 nanometers, and a thickness less than 10 nanometers.

DETAILED DESCRIPTION OF THE EMBODIMENTS

Figure 1:
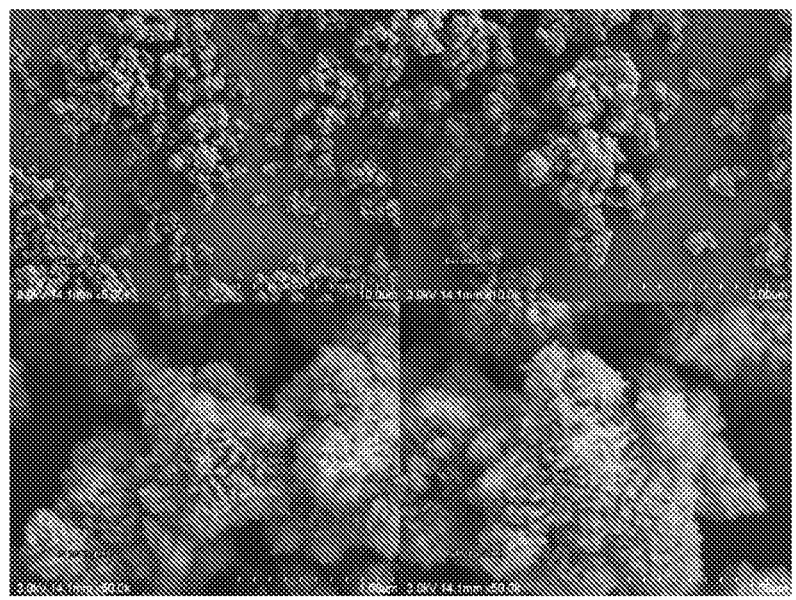
FIG. 1 shows scanning electron micrograph (SEM) images of the high external area zeolite beta of Example 4.

In one aspect, a process is described herein for producing monoalkylated benzenes, such as ethylbenzene and cumene, by contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the transalkylation catalyst composition comprises zeolite beta having an external surface in excess of 350 m²/g as determined by the t-plot method for nitrogen physisorption.

Zeolite beta and one conventional method of its synthesis are described in U.S. Pat. No. 3,308,069, and Re. No. 28,341. Discussion of the framework of beta zeolite may be found in the following references: Higgins et al., "The framework topology of zeolite beta," Zeolites, 8, 446-452 (1988); Newsam et al., "Structural characterization of zeolite beta," Proc. R. Soc. Lond. A, 420, 375-405 (1988); and Blasco et al., "Unseeded synthesis of Al-free Ti-beta zeolite in fluoride medium: A hydrophobic selective oxidation catalyst" Chem. Commun., 2367-2368 (1996).

As conventionally synthesized, zeolite beta has an external surface of less than 300 m²/g as determined by the t-plot method for nitrogen physisorption and has a ratio of external surface area to internal surface area (also referred to as microporous surface area) of less 0.55.

The present transalkylation process employs a transalkylation catalyst composition which comprises a form of zeolite beta that has an unusually high external surface area in excess of 350 m²/g, such as at least 400 m²/g, and/or an external surface area of at most 650 m²/g, such as at most 600 m²/g, all as determined by the t-plot method for nitrogen physisorption. In some embodiments, the zeolite beta employed herein has a ratio of external surface area to internal or microporous surface area of at least 0.6, such as at least 0.8, such as at least 1.0, for example at least 1.1, even at least 1.2. In particular, although zeolite beta catalysts are able convert to convert dialkylbenzenes very effectively, their ability to convert trialkylbenzenes is more limited. However, it has now been found that, by reducing the crystal size of the zeolite beta, a higher conversion of trialkylbenzene to monoalkylbenzene can be achieved. While not wishing to be bound by any theory of operation, it is believed that by reducing the crystal size, the external surface area of the zeolite beta is increase, enabling a higher rate of diffusion and therefor reaction rate of the trialkylbenzenes. This higher conversion of trialkylbenzene compounds can be utilized to enable a more efficient transalkylation process by reducing the recycle rate of trialkylbenzenes, and hence reducing the amount trialkylbenzenes that must be redistilled. Alternatively, the higher activity beta catalyst can enable a lower catalyst loading in the transalkylation reactor while achieving the same trialkylbenzene conversion, thereby reducing catalyst costs.

In some embodiments, the zeolite beta of the transalkylation catalyst composition employed in the present transalkylation process comprises crystals having all dimensions less than or equal to 150 nanometers, such as a length from 50 nanometers to 150 nanometers, a width from 6 nanometers to 15 nanometers, and a thickness less than 10 nanometers. It will be appreciated that such dimensions refer to the dimensions of the individual crystallites even though in some embodiments the crystallites may be agglomerated into larger particles.

In some embodiments, the zeolite beta of the transalkylation catalyst composition employed in the present transalkylation process comprises an aluminosilicate having a Si/Al molar ratio of at least 15, such as at least 20, such as at least 25 and at most 120, such as at most 100, such as at most 80, for example at most 50. As an example, the Si/Al ratio of the zeolite beta can be from 15 to 120, for example from 20 to 70, such as from 25 to 50.

The high external surface area (HESA) zeolite beta employed herein can be produced by reacting am aqueous mixture comprising a source of aluminum (e.g., aluminum isopropoxide) and a source of silicon (e.g., tetramethylorthosilicate) in the presence of a structure directing agent (SDA) have the formula (I):

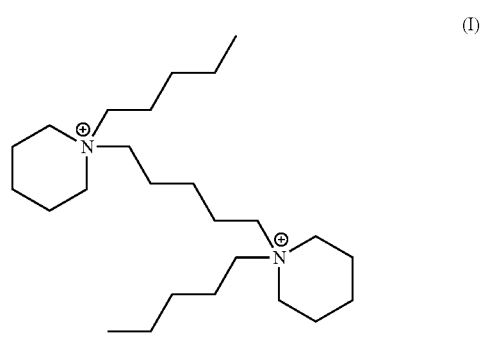 [SMILES: CCCCC[N+]1(CCCCC[N+]2(CCCCC)CCCCC2)CCCCC1]

where the SDA in typically in its hydroxide form. The reaction is generally conducted in an autoclave under tumbling conditions at a temperature of about 130° C. to 180° C. for an appropriate time up to 30 days, for example from 10 days to 30 days. The solid product is recovered (e.g., by filtration) and washed (e.g., with deionized water). The washed product is then dried (e.g., in an oven at from 50° C. to 100° C.). Organic material (e.g., remaining SDA) is removed from the zeolite by heating (e.g., at a temperature of 500° C. to 800° C.). More details of the synthesis procedure, including preparation of the SDA of formula (I), can be found in, for example, International Patent Publication No. WO 2018/236471.

In addition, to HESA zeolite beta, the catalyst employed in the present transalkylation process may comprise one of more additional molecular sieves, especially large pore molecular sieves having a Constraint Index less than 2. Suitable large pore molecular sieves include zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Another class of molecular sieve materials which may be used in combination with HESA zeolite beta in the present transalkylation catalyst is the group of mesoporous crystalline materials exemplified by the MCM-41 and MCM-48 materials. These mesoporous crystalline materials are described in U.S. Pat. Nos. 5,098,684; 5,102,643; and 5,198,203. MCM-41, which is described in U.S. Pat. No. 5,098, 684, is characterized by a microstructure with a uniform, hexagonal arrangement of pores with diameters of at least about 1.3 nm: after calcination it exhibits an X-ray diffraction pattern with at least one d-spacing greater than about 1.8 nm and a hexagonal electron diffraction pattern that can be indexed with a d100 value greater than about 1.8 nm which corresponds to the d-spacing of the peak in the X-ray diffraction pattern. The preferred catalytic form of this material is the aluminosilicate although other metallosilicates may also be utilized. MCM-48 has a cubic structure and may be made by a similar preparative procedure Other suitable molecular sieves for use in the present transalkylation catalyst in addition to HESA zeolite beta include molecular sieves of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513) and mixtures thereof.

The above molecular sieves may be used as the transalkylation alkylation catalyst without any binder or matrix, i.e., in so-called self-bound form. Alternatively, the molecular sieve(s) may be composited with another material which is resistant to the temperatures and other conditions employed in the alkylation reaction. Such binder materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. Preferred binder materials may be selected from the group consisting of alumina, clay, silica, and/or metal oxides. The relative proportions of molecular sieve and binder may vary widely, with the sieve content ranging from about 1 to about 90 weight % and more usually with the zeolite/binder weight ratio in the catalyst composition being from 20/80 to about 80/20.

Suitable conditions for the transalkylation of both polyethylbenzenes and polyisopropylbenzenes with benzene over the present zeolite beta catalyst include a temperature of 100° C. to 300° C., a pressure of 696 kPa-a to 5100 kPa-a, a weight hourly space velocity of 0.5 to 200 $hr^{-1}$ based on the weight of polyalkylated aromatic compounds and a benzene/polyalkylate weight ratio 0.5:1 to 20:1. Preferred conditions include a temperature of 150° C. to 260° C., a pressure of 696 kPa-a to 4137 kPa-a, a weight hourly space velocity of 0.5 to 100 $hr^{-1}$ based on the weight of polyalkylated aromatic compounds and benzene/polyalkylate weight ratio 1:1 to 10:1. In one preferred embodiment, where the transalkylation feed comprises diisopropylbenzene and triisopropylbenzene and the desired monoalkylated product comprises cumene, the transalkylation conditions comprise a temperature in the range of 140 to 240° C. Typically, the transalkylation conditions are controlled such that the polyalkylated aromatic compounds and the benzene are at least partially or predominantly in the liquid phase.

Depending on the composition of the transalkylation feed and the transalkylation conditions employed, it is found that the HESA zeolite beta catalyst employed herein is effective in converting at least 40% by weight, preferably at least 50% by weight, of dialkylated benzene in the feed to the equivalent monoalkylated product, typically with the weight ratio of the conversion of trialkylated benzene to the conversion of dialkylated benzene being at least 0.2, such as from 0.2 to 2, for example 0.2 to 1.2.

Any mixture of dialkylated and trialkylated benzenes can be used in the present transalkylation process, although in most practical embodiments the polyalkylated benzene feedstock used herein will comprise part or all of the heavy fraction remaining after separation of a desired monoalkylated product, especially ethylbenzene or cumene, from the reaction effluent of the alkylation of benzene with an alkylating agent, especially a $C_2$ or $C_3$ alkylating agent. In such a case, the polyalkylated benzene feedstock will typically contain from 40% by weight to 85% by weight of the dialkylated benzene and from 5% by weight to 60% by weight, or from 15% by weight to 60% by weight, of the trialkylated benzene.

Thus, in a further aspect, the present invention relates to a process for producing a monoalkylated benzene, in which a feedstream comprising benzene is initially contacted with an alkylating agent in the presence of an alkylation catalyst composition under alkylation conditions effective to convert at least part of the benzene in the feedstream to the desired monoalkylated benzene and produce an alkylation effluent comprising monoalkylated benzene, dialkylated benzene and trialkylated benzene. The alkylation effluent is then separated into a first fraction containing the monoalkylated benzene and a second fraction containing the dialkylated benzene and the trialkylated benzene. At least part of the second fraction is then contacted with additional benzene in the presence of the transalkylation catalyst composition as described above to convert at least part of the dialkylated benzene and trialkylated benzene to monoalkylated benzene and produce a transalkylation effluent, from which the monoalkylated benzene can be recovered.

The above process can find utility with a wide range of alkylating agents, but has particular advantage with $C_2$ and $C_3$ alkylating agents. Suitable alkylating agents are olefins and alcohols, which may be linear, branched or cyclic. In some embodiments, the alkylating agent is a $C_2$ alkylating agent, such as ethylene, or a $C_3$ alkylating agent, such as propylene and/or isopropanol. Preferably, the alkylating agent comprises propylene and/or isopropanol and the desired monoalkylated benzene product comprises cumene.

Suitable alkylation catalyst compositions comprises any or all of the molecular sieves discussed above in relation to the transalkylation catalyst, including zeolite beta whether in its conventional or HESA forms. In addition, the alkylation catalyst may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. Preferred alkylation catalysts comprise zeolite beta or a zeolite of the MCM-22 family. The above molecular sieves may be used as the alkylation catalyst without any binder or matrix or can be combined with any of the binder materials discussed above as suitable for use in the transalkylation catalyst.

The reaction conditions used to conduct the alkylation step will depend on the particular alkylating agent employed, but suitable conditions are well within the ambit of anyone of ordinary skill in the art. For example, alkylation of benzene with ethylene to produce ethylbenzene is typically conducted at a temperature about 120° C. to 300° C., preferably, a temperature of from about 150° C. to 260° C., a pressure of 500 to 8300 kPa-a, preferably, a pressure of 1500 to 4500 kPa-a, so that at least part of the reaction mixture is maintained in the liquid phase during the process. Generally, the molar ratio of benzene to ethylene is from about 1 to about 100, preferably from about 20 to about 80. In the case of alkylation of benzene with propylene to produce cumene, typical reaction conditions include a temperature of about 20° C. to about 350° C., for example about 50° C. to about 300° C., such as about 100° C. to about 280° C., and a pressure of about 100 kPa to about 20,000 kPa, for example about 500 kPa to about 10,000 kPa, so that at least part of the reaction mixture is maintained in the liquid phase during the process. Generally, the molar ratio of benzene to propylene is maintained within the range of about 1:1 to about 30:1, typically from 1.1:1 to 10:1.

In addition to the desired monoalkylated aromatic product, the effluent from the main alkylation reaction may contain significant quantities of unreacted benzene, together with smaller quantities of polyalkylated species, for example diisopropylbenzene (DIPB) and some triisopropylbenzene (TIPB) in a cumene process, and diethylbenzene (DEB) and some triethylbenzene (TEB) in an ethylbenzene process. The effluent from the main alkylation reaction is therefore fed to a separation system to allow recovery of the monoalkylated aromatic product and further processing of the by-products and impurities.

The separation system may include one or more benzene distillation columns, where unreacted benzene may be removed from the effluent as an overhead or side stream for recycle to the alkylation reaction and/or to the transalkylation reactor (as described above). The bottoms from the benzene column(s) can then be fed to one or more monoalkylate distillation columns to recover the desired monoalkylated aromatic product. The bottoms from the monoalkylate column(s) contain the majority of the byproducts of the alkylation reaction heavier than the desired monoalkylate product. This bottoms stream may then be fed to one or more polyalkylate distillation columns to separate a polyalkylated aromatic product stream containing most of the dialkylated by-product and part of the trialkylated by-product for passage to the transalkylation reaction. The remainder of the trialkylated by-product and essentially all of the compounds heavier than the trialkylated by-product may be discharged at the bottoms of the polyalkylate column as residue.

The term "impurities" as used herein includes, but is not limited to, compounds having at least one of the following elements: nitrogen, halogens, oxygen, sulfur, arsenic, selenium, tellurium, phosphorus, and Group 1 through Group 12 metals.

In some embodiments, where the benzene feedstream to the alkylation and/or transalkylation reaction comprises impurities, the process further comprises: contacting the benzene feedstream with an absorbent under conditions effective to remove at least part of the impurities. The adsorbent may have catalytic activity and may comprise a molecular sieve, such as any of the molecular sieves described above, and a small quantity of alkylating agent may be simultaneously fed to the adsorbent to react with the benzene feed and thereby act as a marker for poison capacity of the adsorbent.

The invention will now be more particularly described with reference to the following non-limiting Examples and the accompanying drawings.

Example 1 (Comparative): Preparation of 80% Beta/20% Siral Catalyst

Conventional, low external surface area zeolite beta produced according to U.S. Pat. No. 5,164,170 was extruded with an alumina binder supplied by Sasol North America under the tradename Siral-30 at an 80/20 beta/binder weight ratio into a 1/20" quadrolobe shape. The product was predried in flowing $N_2$ at 925° F. (496° C.), exchanged with ammonium nitrate, and calcined at 1000° F. (538° C.) under air.

Example 2 (Comparative): Preparation of 40% Beta/40% Meso-MOR/20% Versal-300 Catalyst A mixture of the zeolite beta of Example 1, mesoporous mordenite produced as described in U.S. patent Ser. No. 10/017,394, and an alumina binder supplied by Honeywell UOP under the tradename Versal-300 having the formulation given above was extruded into a 1/20" quadrolobe shape. The product was predried in flowing $N_2$ at 925° F. (496° C.), exchanged with ammonium nitrate, and calcined at 1000° F. (538° C.) under air.

Example 3 (Comparative): Preparation of 40% Beta/40% MCM-41/20% Versal-300 Catalyst A mixture of the zeolite beta of Example 1, MCM-41 produced as described in U.S. Pat. No. 5,098,684 and a Versal 300 alumina binder having the formulation above was extruded into a 1/20" quadrolobe shape. The product was predried in flowing $N_2$ at 925° F. (496° C.), exchanged with ammonium nitrate, and calcined at 1000° F. (538° C.) under air.

Example 4: Preparation of 65% High External Surface Area (HESA) Beta/35% Versal-300 Catalyst High external surface area (HESA) zeolite beta was produced using the following synthesis regime.

Within a tared vessel, 1.35 grams aluminum isopropoxide was dissolved in 73.7 grams of a solution of 1,1'-(pentane-1,5-diyl)bis(1-pentylpiperidine) in its hydroxide form ([OH—]=0.68 millimole/gram). 15.23 grams of tetramethylorthosilicate was then added to the mixture and the resulting mixture was stirred thoroughly. At this point, the suspension was placed within a vented fume hood over the course of three days to allow the complete hydrolysis of the silica and alumina sources and to allow evaporation of water and the resultant methanol from the hydrolysis. At this point, deionized water was added to the suspension to bring the molar H2O/SiO2 ratio to 20. The mixture was then placed within a 125 milliliter Teflon liner, which was capped and then placed inside a sealed steel Parr autoclave. The autoclave was placed within a convection oven at 150° C. under tumbling conditions. After 21 days, the reactor was removed from the oven and quenched to room temperature. The solid product was recovered by filtration and washed with 1000 milliliters of deionized water. The product was then dried in an oven at 80° C. Powder XRD showed the material to be zeolite beta with very broad peaks in the pattern. The organic directing agent was removed from the zeolite by calcination to 600° C.

Table 1 compares the properties of the resultant HESA zeolite beta with those of the zeolite beta of Example 1, the mesoporous mordenite of Example 2, and the MCM-41 of Example 3. SEM images of the HESA zeolite beta product at various magnifications are shown in FIG. 1.

TABLE 1

| Catalyst | BET Total ($m^2/g$) | Micropore Surface Area ($m^2/g$) | External Surface Area ($m^2/g$) | External/ Micro Ratio | Crystal Size (μm) | Si:Al$_2$ (molar) |
|---|---|---|---|---|---|---|
| Example 4 | 765 | 342 | 423 | 1.23 | 0.005-0.15 | 40 |
| Example 1 | 791 | 521 | 270 | 0.518 | 0.2-10 | 27 |
| Example 2 | 585 | 383 | 201 | 0.525 | 0.2-10 | 23 |
| Example 3 | 651 | 482 | 169 | 0.351 | 0.2-10 | 31 |

The resultant HESA zeolite beta was mixed with Versal 300 binder in the proportions listed above and extruded into a 1/16" quadrolobe shape. The extrudate was predried in flowing $N_2$ at 925° F. (496° C.), exchanged with ammonium nitrate, and calcined at 1000° F. (538° C.) under air.

Example 5: Catalyst Testing in DIPB/TIPB Transalkylation

Figure 2:
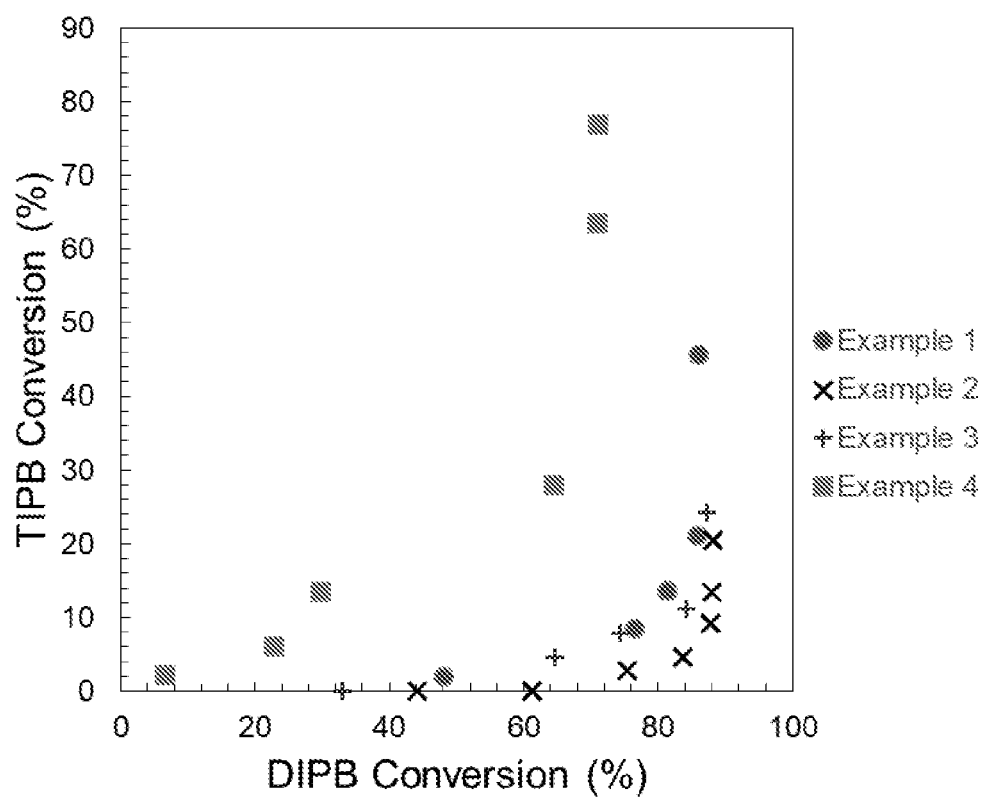
FIG. 2 is a graph plotting triisopropylbenzene (TIPB) conversion against diisopropylbenzene (DIPB) conversion for the catalysts of Examples 1 to 4 when tested under the conditions of Example 5.
Figure 3:
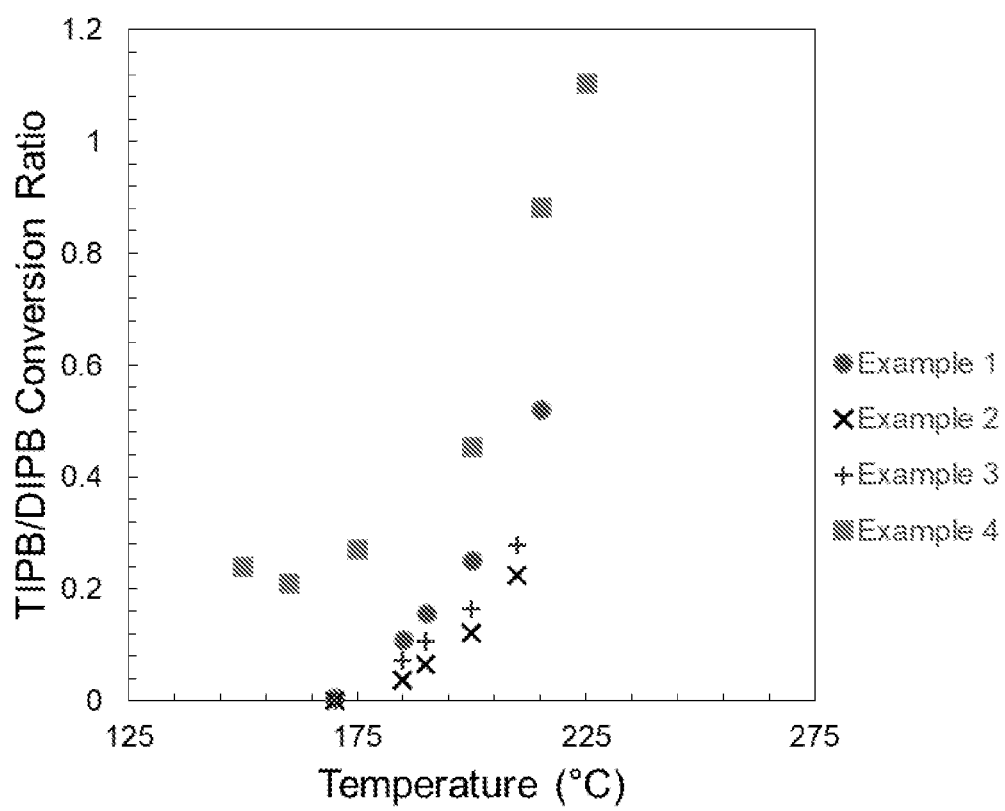
FIG. 3 is a graph plotting TIPB/DIPB conversion ratio against temperature for the catalysts of Examples 1 to 4 when tested under the conditions of Example 5.

A series of tests were run in which a mixture comprising 50 wt % benzene, 30 wt % DIPB and 10 wt % TIPB was contacted separately with each of the catalysts of Examples 1 to 4 at a pressure of 2070 kPa-a and at various temperatures between 150 and 230° C. and the DIPB and TIPB conversions were measured for each run. The results are shown in FIGS. 2 and 3 and show that that the HESA zeolite beta catalyst of Example 4 consistently exhibited a TIPB/DIPB conversion ratio in excess of 0.2 over the whole range of temperatures tested, with the ratio being above 1.0 at the higher temperatures. Also at the higher temperatures the catalyst of Example 4 exhibited TIPB conversion of about 65 to 75% by weight and DIPB conversion in excess of 60% by weight. In contrast, with the catalysts of Examples 1 to 3, in one only run (the catalyst of Example 1 at 220° C.) did the TIPB/DIPB conversion ratio exceed 0.5, with all the other runs giving TIPB/DIPB conversion ratios below 0.3 and generally below 0.2. Moreover, in most runs with the catalysts of Examples 1 to 3, the TIPB conversion level was below 40% by weight.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention

The invention claimed is:

1. A process for producing a monoalkylated benzene comprising the step of contacting benzene with a mixture comprising dialkylated and trialkylated benzenes in the presence of a transalkylation catalyst composition under transalkylation conditions effective to convert at least part of the dialkylated and trialkylated benzene to monoalkylated benzene, wherein the transalkylation catalyst composition comprises zeolite beta having an external surface in excess of 350 $m^2/g$ as determined by the t-plot method for nitrogen physisorption, and wherein the zeolite beta has a ratio of external surface area to internal surface area of at least 0.6.

2. The process of claim 1, wherein the zeolite beta has an external surface area of at least 400 $m^2/g$ as determined by the t-plot method for nitrogen physisorption.

3. The process of claim 1, wherein the zeolite beta comprises crystals having a length from 50 nanometers to 150 nanometers, a width from 6 nanometers to 15 nanometers, and a thickness less than 10 nanometers.

4. The process of claim 1, wherein the transalkylation conditions are such that the weight ratio of the conversion of trialkylated benzene to the conversion of dialkylated benzene is at least 0.2.

5. The process of claim 1, wherein the transalkylation conditions are such that the weight ratio of the conversion of trialkylated benzene to the conversion of dialkylated benzene is in the range of 0.5 to 2.

6. The process of claim 1, wherein the transalkylation conditions are such that the conversion of dialkylated benzene is at least 40% by weight.

7. The process of claim 1, wherein the monoalkylated benzene comprises cumene.

8. The process of claim 1, wherein the transalkylation conditions comprise a temperature in the range of 140 to 240° C.

9. The process of claim 1, wherein the transalkylation catalyst composition further comprises a binder selected from the group consisting of alumina, clay, silica, and/or metal oxides, wherein the zeolite/binder weight ratio in said catalyst composition is from 20/80 to about 80/20.

10. The process of claim 1, wherein the transalkylation conditions are such that the conversion of trialkylated benzene is at least 60% by weight.

11. A process for producing a monoalkylated benzene, the process comprising:
(a) contacting a feedstream comprising benzene with an alkylating agent in the presence of an alkylation catalyst composition under alkylation conditions effective to convert at least pan of the benzene in the feedstream to the desired monoalkylated benzene and produce an alkylation effluent comprising monoalkylated benzene, dialkylatedbenzene and trialkylatedbenzene;
(b) separating the alkylation effluent into a first fraction containing monoalkylated benzene and a second fraction containing dialkylatedbenzene and trialkylatedbenzene;
(c) contacting at least part of the second fraction with benzene in the presence of a transalkylation catalyst composition under transalkylation conditions effective to convert at least part of the dialkylatedbenzene and trialkylatedbenzene to monoalkylated benzene and produce a transalkylation effluent, wherein the transalkylation catalyst composition comprises zeolite beta having one or more of the following properties:
(i) an external surface in excess of 350 m$^2$/g as determined by the t-plot method for nitrogen physisorption,
(ii) a ratio of external surface area to internal surface area of at least 0.6, and
(iii) a length from 50 nanometers to 150 nanometers, a width from six nanometers to 15 nanometers, and a thickness less than 10 nanometers; and
(d) recovering the monoalkylated benzene from the transalkylation effluent.

12. The process of claim 11, wherein the alkylation catalyst composition comprises a zeolite selected from the group consisting of beta faujasite, mordenite or a zeolite of the MCM-22 family.

13. The process of claim 11, wherein the zeolite beta of the transalkylation catalyst composition has an external surface area of at least 450 m$^2$/g as determined by the t-plot method for nitrogen physisorption.

14. The process of claim 11, wherein the transalkylation conditions are such that the weight ratio of the conversion of trialkylated benzene to the conversion of dialkylated benzene is at least 0.2.

15. The process of claim 11, wherein the transalkylation conditions are such that the weight ratio of the conversion of trialkylatedlbenzene to the conversion of dialkylatedbenzene is in the range of 0.5 to 2.

16. The process of claim 11, wherein the transalkylation conditions are such that the conversion of dialkylatedbenzene is at least 40% by weight.

17. The process of claim 11, wherein the monoalkylated benzene is ethylbenzene or cumene.

18. The process of claim 11, wherein the monoalkylated benzene is cumene and the alkylating agent comprises propylene and/or isopropanol.

19. The process of claim 11, wherein the transalkylation conditions comprise a temperature in the range of 140 to 240° C.

20. The process of claim 11, wherein the transalkylation catalyst composition further comprises a binder selected from the group consisting of alumina, clay, silica, and/or metal oxides, wherein the zeolite/binder weight ratio in said catalyst composition is from 20/80 to about 80/20.

21. The process of claim 11, wherein the alkylation effluent further comprises unreacted benzene and the process further comprises:
(e) separating the unreacted benzene from the alkylation effluent and recycling at least part of the unreacted benzene to the contacting (a), the contacting (c), or both.

22. The process of claim 11, wherein the transalkylation effluent further comprises unreacted benzene and the process further comprises:
(f) separating the unreacted benzene from the transalkylation effluent and recycling at least part of the unreacted benzene to the contacting (a), the contacting (c), or both.

23. The process of claim 11, wherein the feedstream further comprises impurities and the process further comprises:
(g) contacting the feedstream with an absorbent under conditions effective to remove at least part of the impurities, wherein the impurities comprise compounds having at least one of the following elements: nitrogen, halogens, oxygen, sulfur, arsenic, selenium, tellurium, phosphorus, and Group 1 through Group 12 metals.

* * * * *